United States Patent [19]

Tucker

[11] Patent Number: 4,796,627
[45] Date of Patent: Jan. 10, 1989

[54] CLIP APPLICATOR AND SPREADABLE CLIPS FOR USE THEREIN

[76] Inventor: Wilson H. Tucker, Box 265, R.D. 1, Mystic, Conn. 06355

[21] Appl. No.: 900,383

[22] Filed: Aug. 26, 1986

[51] Int. Cl.$^4$ .............................................. A61B 17/08
[52] U.S. Cl. ..................................... 128/337; 128/346
[58] Field of Search ........... 128/325, 326, 330, 334 R, 128/334 C, 335, 337, 346; 72/410; 227/DIG. 1; 29/243.56; 206/339–343; 24/456, 503, 545, 546, 547, 563, 555

[56] References Cited

U.S. PATENT DOCUMENTS

| 733,723 | 7/1903 | Lukens | 128/337 |
|---|---|---|---|
| 3,209,754 | 10/1965 | Brown | 128/337 |
| 3,446,212 | 5/1969 | Le Roy | 128/337 |
| 3,604,425 | 9/1971 | Le Roy | 128/346 |
| 4,512,345 | 4/1985 | Green | 128/325 |
| 4,557,263 | 12/1985 | Green | 128/325 |
| 4,612,932 | 9/1986 | Caspar | 128/334 |
| 4,637,395 | 1/1987 | Caspar et al. | 128/346 |
| 4,671,278 | 6/1987 | Chin | 128/325 |

Primary Examiner—Dalton L. Truluck
Attorney, Agent, or Firm—Victor E. Libert

[57] ABSTRACT

An applicator for the manual application of spreadable surgical clips which comprises a clip magazine which releasably retains a plurality of spreadable clips and forms a guideway for the clips, e.g., it may optionally include a pair of spaced-apart, parallel rail members extending throgh the magazine to slidably carry the clips. A spreader at the discharge end of the clip magazine, e.g., a pair of optionally bifurcated, wedge-shaped ramps, serves to receive and spread apart the clips for ejection of the spread-apart clips from the applicator.

Spreadable surgical clips are also provided. The clips may have a front-to-rear taper to clear the discharge end of the applicator. The clips may have front connecting means and rear connecting means to disengageably connect the clips in a train of clips within the applicator. Generally, the clips may comprise a tubular body having a front-to-rear taper and a longitudinally extending clamping slit along the length of the body, to define opposing leg portions.

12 Claims, 3 Drawing Sheets

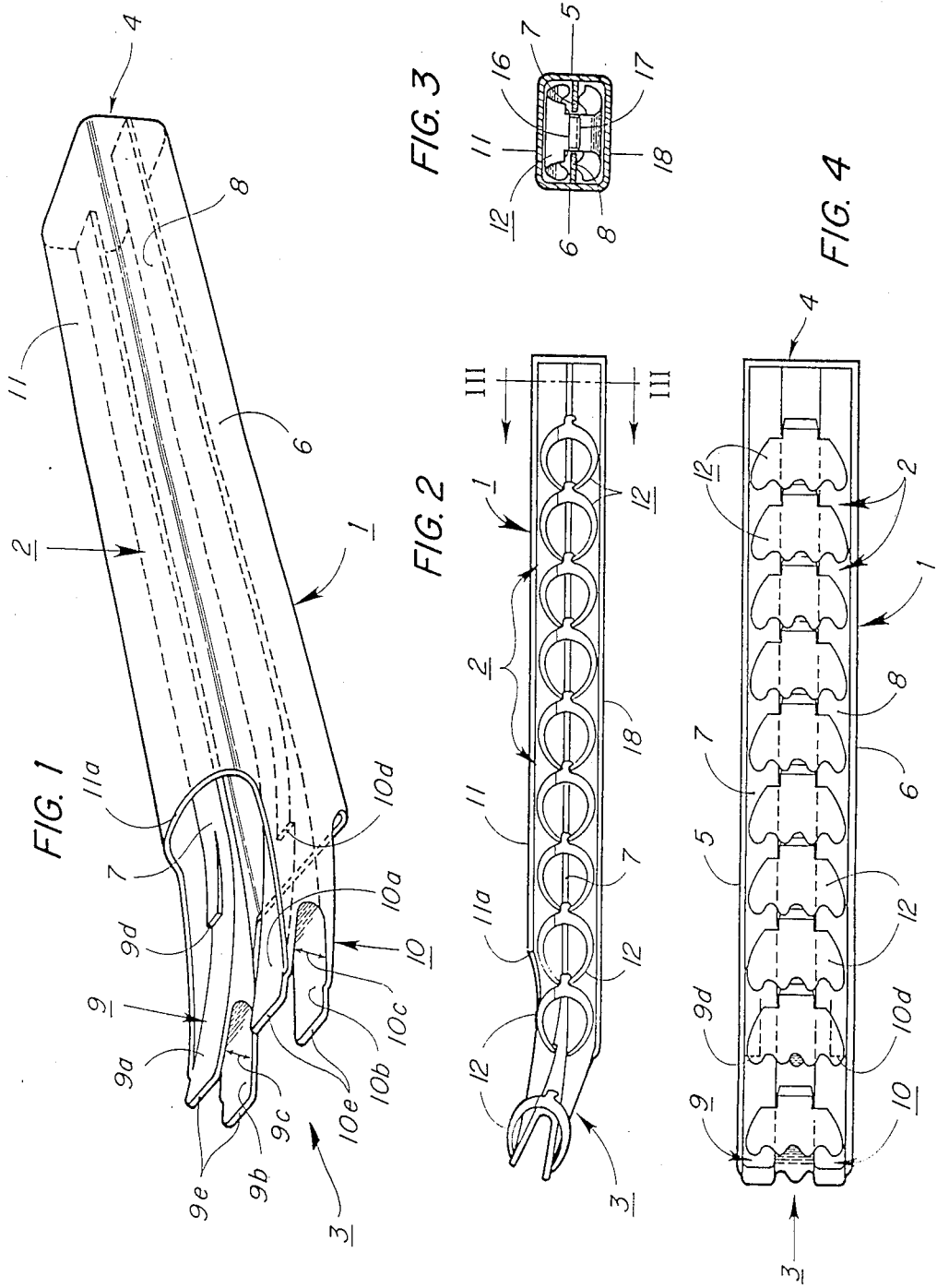

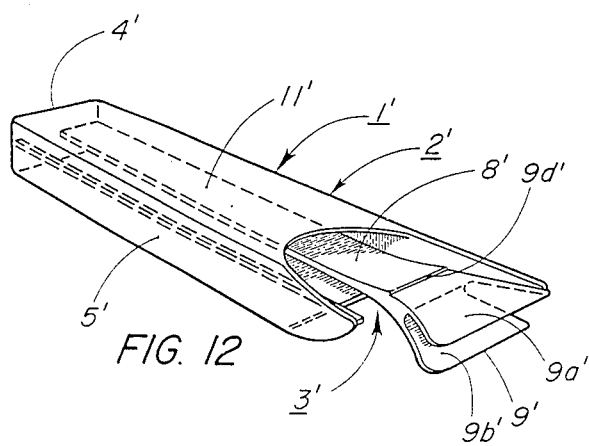
FIG. 12
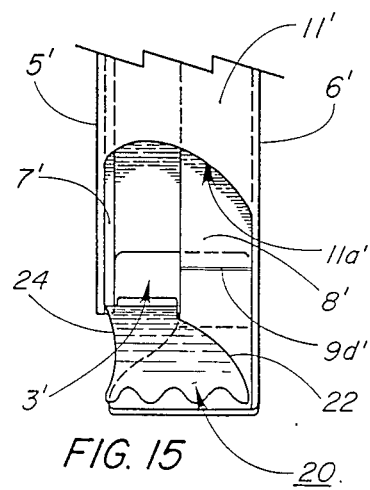
FIG. 15
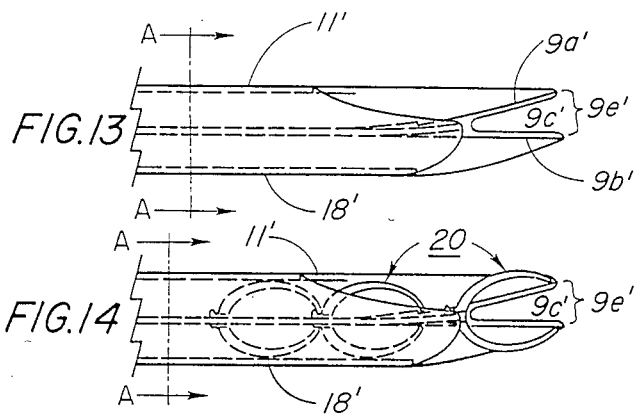
FIG. 13
FIG. 14
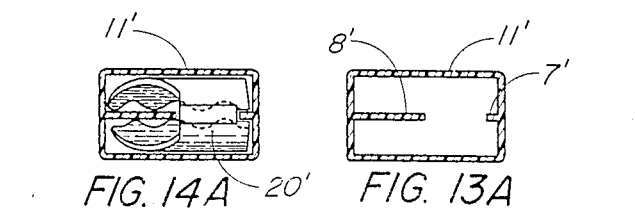
FIG. 14A
FIG. 13A
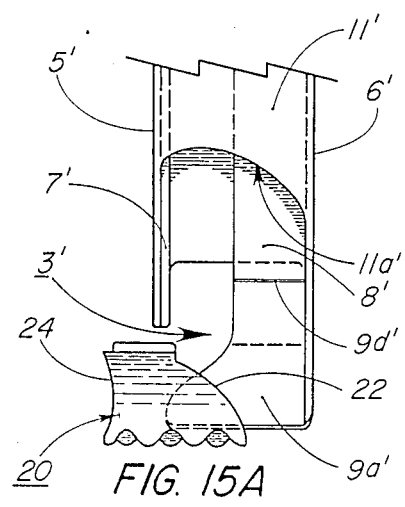
FIG. 15A
FIG. 17
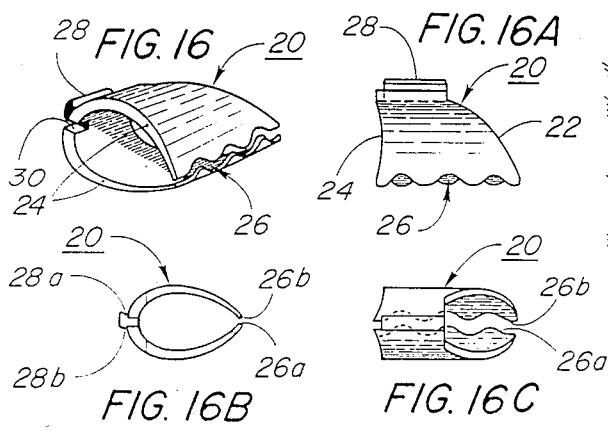
FIG. 16
FIG. 16A
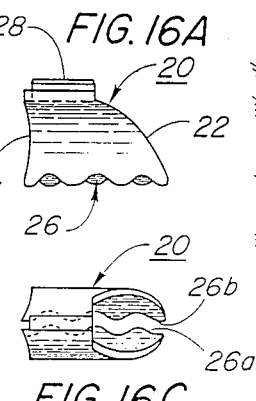
FIG. 16B
FIG. 16C
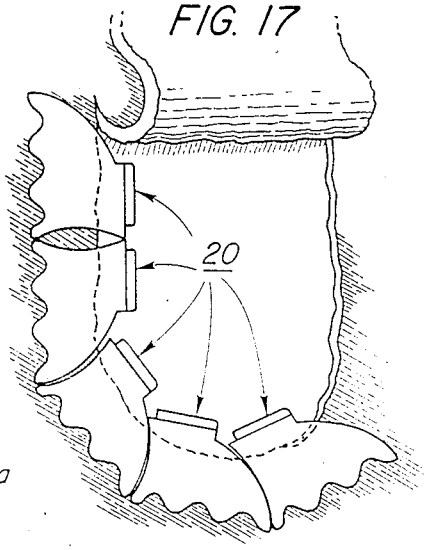

CLIP APPLICATOR AND SPREADABLE CLIPS FOR USE THEREIN

BACKGROUND OF THE INVENTION

1. Field Of The Invention

The present invention relates to a novel and improved applicator for applying spreadable clips, especially surgical clips such as hemostatic clips and wound clasps, to a wound or incision, and to novel and improved spreadable clips therefor.

2. Description Of The Related Art

Spreadable clips, especially spreadable surgical clips, and applicators for applying them to a wound or incision are well known in the art. For example, U.S. Pat. No. 3,098,232 issued July 23, 1963 to A. M. Brown discloses a surgical clip applicator for closing a wound or incision by applying thereto crimpable, U-shaped clips. The applicator has two sections which pivot about hinges between a closed position and an open position. A magazine of crimpable clips is loaded into a guideway by means of an applicator rod (74) which is withdrawn after the instrument is closed to leave behind the clips. Arms 54, 56 (FIG. 14) are compressed to crimp an individual clip from its shape shown in FIG. 8 to that shown in FIG. 9 in order to apply it to the incision as shown in FIG. 21. The patentee also discloses a separate tool (FIGS. 25 and 26) for removing the clips after the incision has healed.

U.S. Pat. No. 4,217,902 issued Aug. 19, 1980 to A. L. March discloses resilient hemostatic clips having a longitudinally extending U-shaped depression which serves as a hinge-like structure about which the legs of the clip may be spread and then released for clamping an incision. Several embodiments are illustrated and each utilizes the conventional technique of employing pliers to spread the clip for application, and to allow the clip to close, by reason of its resiliency, to its clamping position upon release of the pliers. Means, such as apertures, are provided on the clip for cooperating with the pliers.

U.S Pat. No. 4,372,316 issued Feb. 8, 1983 to J. W. Blake, III, et al discloses a surgical clip applicator essentially comprising a forceps between the jaws of which a cartridge is positioned to feed surgical suturing clips to the jaws. Individual clips are fed into the anvil tip 30 of the forceps and, as described at column 5, line 65 et seq of the patent, each individual U-shaped clip is crimped to a closed position as shown in FIG. 11C in order to clamp off, e.g., a blood vessel. Opening of the forceps feeds the next clip into the anvil tip.

U.S. Pat. No. 4,522,207 issued June 11, 1985 to C. H. Klieman et al discloses a hemostatic clip applicator in which a train of U-shaped clips 37 are fed by a ratchet means operated by movement of finger loops 4, 6 into the jaws 32, 34 (FIG. 1). As described at column 10, line 29 et seq and column 11, line 23 et seq, further operation of the finger loops crimps the surgical clip 37' held between the jaws.

SUMMARY OF THE INVENTION

In accordance with the present invention there is provided an applicator for the manual application of spreadable surgical clips. The applicator comprises a clip magazine having a clip discharge section and dimensioned and configured to releasably retain therein, and form a guideway for, a plurality of spreadable clips, and a spreader comprising one or more ramps which are dimensioned and configured to receive in slidable engagement thereon for ejection therefrom spreadable clips from the clip magazine. For example, the spreader may comprise a pair of laterally spaced-apart bifurcated ramps which provide clearance for passage of the clips therebetween, or it may comprise a single bifurcated ramp which is laterally off-set from the longitudinal axis of the applicator. In any case, the spreader has an inlet section disposed adjacent to the clip discharge section of the magazine and a discharge tip which is wider in the clip-spreading direction than its inlet section, so that the spreader has a wedge-shaped profile. With this construction, dislodgement of the spreadable clips from the magazine onto the spreader spreads the dislodged clip for ejection of the spread clip over the discharge tip of the spreader.

Another aspect of the invention provides for an applicator as described above wherein the longtudinal axis of the spreader defines a discharge axis and the longitudinal axis of the guideway defines a transport axis, and the discharge axis diverges from the transport axis whereby to impose a pivoting movement on a clip moved from the transport axis to the discharge axis.

In another aspect of the invention the laterally spaced-apart ramps comprise a pair of ramps extending, respectively, from laterally opposite sides of the storage enclosure. The storage enclosure may comprise a pair of laterally opposite side walls and each of the pair of ramps may extend from a respective one of the side walls.

In another embodiment of the invention, the spreader comprises a single ramp which is laterally off-set from the longitudinal axis of the spreader. In this embodiment, the discharge tip of the spreader may be wider in a direction transverse to the clip-spreading direction than the inlet section of the spreader. Further, in one such realization of the invention, a pair of laterally spaced-apart rail members may extend within the clip magazine and be dimensioned and configured to be slidably engaged by a plurality of spreadable clips to form at least a part of the guideway, and one of the rail members may be contiguous with the laterally off-set ramp.

In another embodiment, bifurcated ramps are provided, the ramps having a positioning recess formed between the two branches thereof. In another embodiment of the invention, the applicator includes a plurality of laterally spaced-apart rail members extending within the clip magazine and dimensioned and configured to be slidably engaged by a plurality of spreadable clips and to form at least a part of the guideway. In yet another aspect of the invention, a plurality of spreadable clips, preferably clips as described below, are mounted seriatim within the clip enclosure.

In another aspect of the invention, there is provided a spreadable surgical clip having a front face and a bight portion, a pair of opposed leg portions extending from the bight portion and terminating at their respective distal ends in respective bearing lips facing each other to define therebetween a clamping slit in the front face of the clip. The improved features of the clip comprises that the bight portion is narrower than the front face whereby longitudinally opposite ends of the front face define spaced-apart mounting surfaces which extend beyond respective longitudinal ends of the bight portion, and the clip has a front-to-rear narrowing taper. In this embodiment of the invention, the front-to-rear narrowing taper may be greater on one lateral side of the clip than on the other, including providing the front-to-rear narrowing taper on only one lateral side of the clip with the other lateral side being untapered. Alternatively, the same front-to-rear narrowing taper may be provided on both lateral sides of the clip.

Still another aspect of the invention provides for a spreadable surgical clip having a front face and a bight portion having a rear face, a pair of opposed leg portions extending from the bight portion and terminating at their respective distal ends in respective bearing lips facing each other to define therebetween a clamping slot in the front face of the clip. The bearing lips may be toothed, e.g., with respective, meshing teeth, or may be dimensioned and configured to define a tongue-and-groove bearing surface between them. The improved feature of the clip comprises that the front face carries front connecting means and the bight portion carries rear connecting means, which front and rear connecting means are respectively dimensioned and configured whereby the rear connecting means of a clip is releasably engagable with the front connecting means of the clip immediately trailing it, so that two or more of the clips may be releasably connected in a train of clips. For example, the front connecting means may comprise at least one bearing lip of a clip or a protruding member (which may be one or more teeth or protrusions formed in the bearing lip or lips) and the rear connecting means may comprise a land protruding from the bight portion. The land may provide a shoulder and/or at least one recess (e.g., a pair of receses) formed in the rear face of the bight portion and adapted to releasably receive therein at least one bearing lip or protruding member.

In another aspect of the invention, there is provided a clip-loaded manual applicator for seriatim application of a plurality of spreadable clips, the applicator being an applicator as described above and, preferably, the plurality of clips being comprised of clips as described above. In one embodiment, the plurality of the clips carried by the applicator are arranged in a train of clips with each clip releasably connected to an adjacent clip. In another embodiment, the spreader of the applicator is dimensioned and configured relative to the rail members whereby to impose a pivoting movement on a clip slidably moved from the rail members onto the spreader, which pivoting movement suffices to disengage the lead clip from the train of clips.

Other aspects and advantages of the invention will become apparent upon reading the following description. The applicator of the invention has a number of advantages over prior art devices. These include the ability to rapidly and precisely apply clips by a hand-operated device fed from a clip magazine without necessity of loading or picking up and mounting individual clips on the device. This is attained by a simple and inexpensive device, which need have no moving parts or even springs or other biasing means.

Reference herein to "surgical" clips or the like, is intended to broadly include clips designed to be applied to human or animal or other tissue in surgical, medical, experimental or other procedures.

BRIEF DESCRIPTION OF THE DRAWINGS

FIG. 1 is a perspective view showing one embodiment of the clip applicator of the present invention, the applicator being shown as empty of clips, for clarity of illustration;

FIG. 2 is a section view in side elevation of the applicator of FIG. 1;

FIG. 3 is a section view taken along line III—III of FIG. 2;

FIG. 4 is a plan view of the applicator of FIG. 1 with the top wall thereof omitted for clarity of illustration;

FIG. 12 is perspective view showing another embodiment of the clip applicator of the present invention, the applicator being shown empty of clips for improved clarity of illustration;

FIG. 13 is a partial side view in elevation showing the front or discharge end of the applicator of FIG. 12;

FIG. 13A is a section view taken along line A—A of FIG. 13;

FIG. 14 is a view corresponding to FIG. 13 but showing the applicator of FIG. 12 with three spreadable clips remaining therein;

FIG. 14A is a section view taken along line A—A of FIG. 14;

FIG. 15 is a partial top plan view showing the front or discharge end of the applicator of FIG. 12 with a single spreadable clip remaining therein and positioned upon the spreader of the applicator;

FIG. 15A is a view corresponding to FIG. 15 showing the clip in the process of being discharged from the spreader of the applicator;

FIG. 16 is perspective view of the front face, untapered lateral side of a spreadable clip in accordance with one aspect of the invention and utilizable by the applicator of FIG. 12;

FIG. 16A is a top plan view of the clip of FIG. 16;

FIG. 16B is a side view in elevation of the tapered side of the clip of FIG. 16;

FIG. 16C is a rear view in elevation of the clip of FIG. 16; and

FIG. 17 shows a plurality of the clips of FIG. 16 mounted about the periphery of a substantially semi-circular incision.

DETAILED DESCRIPTION OF THE PREFERRED EMBODIMENTS

Figure 5:
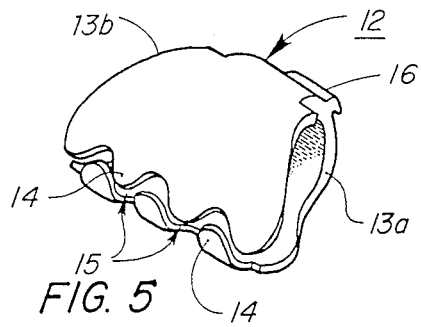
FIG. 5 is a perspective view of the front face of a spreadable clip in accordance with one aspect of the present invention and utilizeable by the applicator of FIG. 1.

The clip applicator of the present invention finds use in a number of applications but is particularly well suited to the application of hemostatic surgical clips to control bleeding during surgery or other procedures. The applicator of the present invention includes a clip magazine for the storage of a supply of spreadable clips and may be provided in a configuration wherein the clip magazine comprises a storage enclosure which can be conveniently and comfortably grasped by a surgeon or other operator when clips are being applied to a wound or incision. A plurality of spreadable clips is arranged seriatim within the clip magazine upon a pair of spaced-apart rail members on which the clips are slidably carried. In use, the clips are pushed by the operator along the rail members to a spreader at the discharge end of the magazine where the clips are spread and dislodged for application one at a time in clamping engagement to a wound or incision. The term "spreadable" clips, as used herein and in the claims, refers to clips which can be spread apart for application to tissue or other material and are sufficiently resilient so that upon release of the spreading force, they close sufficiently to engage or clamp the tissue or material to which they are applied.

Referring now to the drawings, there is illustrated in FIGS. 1-4 an applicator 1 for applying spreadable clips. The applicator 1 comprises a storage enclosure 2 having a discharge end 3, a back wall 4, side walls 5 and 6, top wall 11 and a bottom wall 18. In the illustrated embodiment, storage enclosure 2 is generally rectangular in configuration with rounded corners, but it may be of any shape suitable for the clips to be used therein, e.g., it could be of generally tubular configuration with an oval or circular cross section configuration. An arcuate opening 11a is provided in the top wall 11 of the storage enclosure 2 at the end of top wall 11 which is adjacent to discharge end 3. This opening facilitates manipulation of the clips by the surgeon's thumb as explained more fully below. Storage enclosure 2 is dimensioned and configured to receive a plurality of clips 12 therein. As more fully described below, clips 12 are configured so that they can be releasably engaged one with the other in series to provide a train of clips connected to each other so that pushing the lead clip pulls along the other clips in the train. A pair of rail members 7 and 8 extend in parallel, spaced-apart relationship through the storage enclosure 2 and each terminates at the discharge end 3 of the storage enclosure in a spreader which is provided, in the illustrated embodiment, by respective bifurcated, wedge-shaped ramps 9 and 10 which are laterally spaced-apart from each other. Ramp 9 extends from side wall 5 and ramp 10 extends from side wall 6 so as to provide an open space or passageway between ramps 9 and 10 for passage of the clips therebetween as explained more fully below. Ramps 9 and 10 each divide into two branches, respective upper ramps 9a and 10a and lower ramps 9b and 10b and which terminate in respective discharge tips (9e and 10e). Positioning recesses 9c and 10c are defined between the respective upper and lower ramps 9a, 9b and 10a, 10b to receive therein the edge or lip of the wound to be closed or clamped. In the illustrated embodiment a retainer is provided by step-like structures comprised of retaining lips 9d and 10d, located at a point to engage the clip immediately behind the lead clip (the lead clip being that clip closest to the discharge end 3) at or near the inlet end of the ramps 9 and 10, so as to prevent the train of trailing clips from sliding back away from discharge end 3 when the lead clip is pushed onto ramps 9 and 10 and disengaged from the train of clips. The retainer can be provided by any suitable structure such as a protrusion or recess, e.g., a shoulder, groove or step-like formation suitably positioned, e.g., on the ramps or rail members. Rail members 7, 8 are an optional feature in that the interior walls of storage enclosure 2 may be so dimensioned and configured relative to clips 12 that the interior walls serve as a guideway for slidable movement of clips 12 through storage enclosure 2.

Rail members 7 and 8 may be attached in any suitable manner to the side walls 5, 6 and back wall 4. Alternatively, they may be molded or otherwise integrally formed within the storage enclosure 2. Similarly, ramps 9 and 10 may be molded or otherwise integrally formed as an end or extension of storage enclosure 2, respectively, extending from laterally opposite sides thereof. As illustrated, ramps 9 and 10 are disposed inwardly of their respective associated side wall but are dimensioned to leave an open space or passageway therebetween for passage of the bight portion of the clips, even as longitudinally opposite ends of the clamping slit of the clips engage the ramps 9 and 10.

The applicator of the invention may conveniently comprise an article molded from a suitable plastic material or stamped from metal. Generally, the applicator may be made of any suitable material which is sterilizeable, such as metal, e.g., stainless steel, or a plastic, i.e., a synthetic organic polymeric material. Part or all of the applicator, e.g., the storage enclosure 2 or part thereof, may be slotted or have openings formed therein or made of a transparent or translucent material which is sufficiently transparent to show how many clips remain within the enclosure. The applicator may be economically assembled from two or more readily molded or stamped parts, for example, from two molded plastic parts which are glued or thermally or sonically welded together.

In one embodiment, the applicator may be designed to be re-filled after exhausting its supply of clips. In such case, in order to facilitate loading replacement clips into the storage enclosure, reclosable access means thereto may be provided. For example, in the illustrated embodiment, the back wall 4 may be hinged or otherwise configured to be be openable and re-closeable. In another embodiment, the applicator may be designed to be discarded after its supply of clips is exhausted, instead of being re-filled, sterilized and re-used. In such case, the applicator is preferably made of an inexpensive material such as plastic and may be inexpensively constructed without need for access means for re-loading. Whether designed to be re-fillable or not, back wall 4 could be replaced by tabs or other structures designed to retain the supply of clips 12 within the storage enclosure 2.

Figure 6:
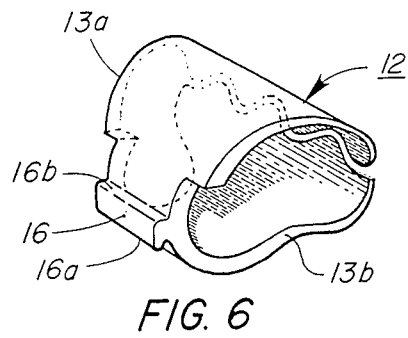
FIG. 6 is a perspective view showing the rear or bight side of the spreadable clip of FIG. 5.
Figure 7:
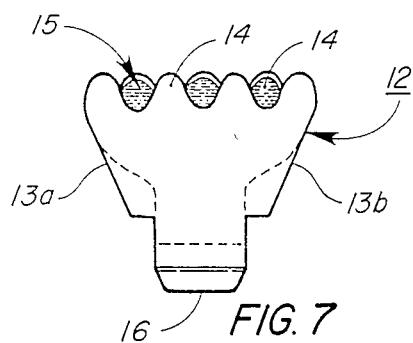
FIG. 7 is a plan view of the spreadable clip of FIG. 5.
Figure 9:
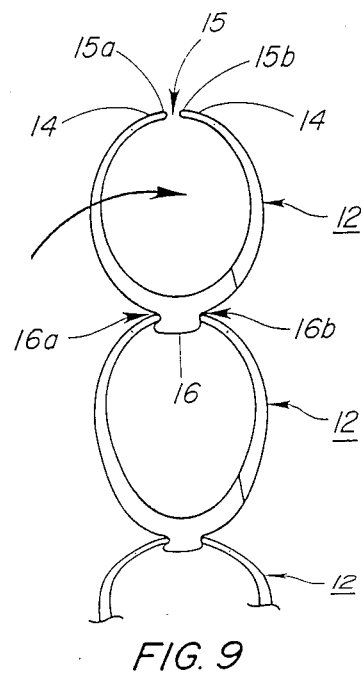
FIG. 9 is a side view showing a plurality of the clips of FIG. 5 releasably engaged with each other, one of the clips being only partially shown.
Figure 8:
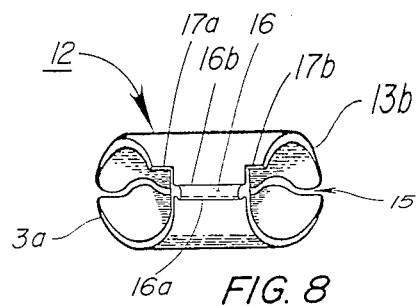
FIG. 8 is a view in elevation showing the rear or bight side of the clip of FIG. 5.

As seen in FIGS. 2, 3 and 4, a train of clips 12 of the type illustrated in FIGS. 5-9 is loaded within storage enclosure 2 in slidable engagement upon the rail members 7, 8. The clips 12 are configured with a front-to-rear decreasing taper so that the outer or opposite side edges of the slit 15 (FIG. 5) in the clips engage respective ones of the rail members, and the narrow rear face or bight portions of the clips 12 ride in the space between rail members 7 and 8. When the clips are pushed onto and eventually off the spreader provided by ramps 9, 10, the bight portions of the clips ride in the space between laterally spaced-apart ramps 9 and 10. FIG. 5 shows one of the spreadable clips 12 which are designed and configured for use with the applicator of the present invention, as shown in FIGS. 2, 3 and 4. Such clips may be made of any suitable resilient material which is sterilizeable, such as a metal, e.g., stainless steel or a plastic, e.g., a synthetic organic polymeric material. Each clip 12 has a generally tubular body having a front-to-rear decreasing taper along the respective side edges 13a and 13b as best seen in FIG. 7. Along the front surface of the clip is a longitudinally extending, tooth-contoured clamping slit 15 which extends along the entire longitudinal length of the body and defines opposed bearing lips 15a, 15b (FIG. 9) which, in the illustrated embodiment, are configured to define teeth 14. The longitudinally opposite ends of bearing lips 15a, 15b comprise engagement or bearing surfaces (unnumbered) which engage the ramps 9 and 10 to thereby spread the clips as they are pushed onto and over the ramps 9 and 10 (FIG. 1). The bearing surfaces of the clips also engage rail members 7, 8 in those embodiments (such as that illustrated) of the applicator which employ such rail members. Since the clip is a spreadable clip, e.g., one made of resilient material, the two opposed, spreadable leg portions on opposite sides of the slit 15 can be spread apart by applying a spreading or separating force thereto, and will close or come back together in a clamping position upon release of the spreading force. On the rear face of the tubular body, in the bight portion of the clip radially opposite the longitudinal slit 15, is formed a land 16 which extends generally longitudinally of clip 12, generally opposite and parallel to the axis along which slit 15 extends. Land 16 has opposite shoulders, one of which is recessed to define a groove 16a and the other of which defines a generally right-angled shoulder 16b, as best shown in FIGS. 6, 8 and 9. The groove 16a and shoulder 16b of each clip are dimensioned and configured to be engaged by respective opposed ones of teeth 14 of the immediately trailing clip, as illustrated in FIGS. 2, 4 and 9. By means of the groove 16a and shoulder 16b, a series of clips 12 may be releasably linked together to form a train of clips slidably mounted on the rail members 7 and 8 as shown in FIGS. 2, 3 and 4. The rear or bight portion (the portion in which land 16 is formed) of the clips 12 is narrower than the front face (the portion in which slot 15 and its teeth 14 are formed) as shown in FIGS. 7 and 8. The bight portion has square-cut corner shoulders 17a and 17b formed at its upper end (as viewed in FIG. 8) in order to help orient and retain each of the clips 12 when it is positioned upon ramps 9, 10 of discharge end 3. Shoulders 17a, 17b respectively engage the top surfaces of upper ramps 9a, 10a to retain the clips securely, but slidably, in place. With this construction, the surgeon or other operator may grasp the applicator 1 with the four fingers of the hand curling about bottom wall 18 and with the tip of the thumb positioned within arcuate opening 11a to push the train of clips towards discharge end 3. As the lead clip is pushed along rail members 7, 8 the remaining clips are pulled along in the interconnected train of clips. This construction eliminates the need for biasing means to push the clips along the rail members to advance them towards the discharge end 3 of the applicator. The clip design in accordance with the invention may be simplified to the extent that it is not necessary to form perforations in the clips through which a rail member or the like is passed to thread the clips on the rail member in order to assure smooth transition from the applicator onto the spreader. The clips may optionally be designed so that in the unstressed condition the bearing lips 15a, 15b, or at least the opposite lateral ends thereof comprising the engagement surface, are spaced slightly apart so as to facilitate engagement with the ramps 9, 10 in cases where rail members 7, 8 are not used.

The lead one of the clips 12 will disengage from the train of clips when it reaches the wedge-shaped ramps 9, 10 at the discharge end 3 of the applicator 1. In the illustrated embodiment the disengagement occurs when the legs of the second clip (the one immediately behind the lead clip) are spread by ramps 9, 10 and/or the lead or front clip is pivoted relative to the second clip by being pushed upon ramps 9, 10. As best seen with reference to FIGS. 1 and 2, ramps 9 and 10 extend along a longitudinal axis (the "discharge axis") which is angled (upwardly, as viewed in FIGS. 1 and 2) relative to the longitudinal axis (the "transport axis") of the guideway along which rail members 7 and 8 extend. By having the discharge end axis diverge at an angle from the transport axis, the lead clip pushed onto the ramps 9, 10 must follow the discharge axis and consequently pivots relative to the train of clips disposed along the transport axis. Disengagement of the teeth 14 of the trailing clip from the land 16 of the lead clip results from the legs of the second clip being spread on ramps 9, 10 and from the lead clip being pivoted relative to the second clip by following the discharge axis. The direction of pivoting motion of the lead clip as it is pushed onto ramps 9, 10 (FIG. 1, 2 and 4) is suggested by the unnumbered arrow in FIG. 9 which well illustrates how a tooth 14 of the second clip will disengage from the groove 16a of the lead clip, and thus disengage from land 16 of the lead clip, as the lead clip pivots to follow the discharge axis of ramps 9, 10. The second clip will be pulled along onto at least the inlet portion of ramps 9, 10 until disengagement of the lead clip from it. The disengaged second clip and the train of clips attached to it may slide or be pushed back to the point where the teeth of the second clip (now the lead clip of the train of clips) are engaged by lips 9d, 10d to hold the train of clips against further backward movement.

While the disengagably connectible clips of the type described herein are preferred for use in the applicator of this invention, it will be appreciated that other type clips may be used in the applicator and that it is not essential that the clips be releasably engagable one to the other in a train of clips.

The clips 12, as viewed in FIG. 4, are centered between the two rail members 7 and 8 which form a guideway for slidably carrying the spreadable clips through the magazine or storage enclosure. The interior of the storage enclosure 2 is dimensioned and configured to clear or slidably engage the clips 12 to allow easy sliding movement therethrough upon rail members 7 and 8. In the latter case, as noted above, rail members 7 and 8 may be omitted. Additionally, the outside dimensions of the storage enclosure 2 are preferably sized to conveniently and comfortably fit in the hand of a surgeon or other operator for easy application of the clips to a wound.

In use, storage enclosure 2 is grasped within the closed palm of a surgeon or operator whose thumb is positioned over the top wall 11 with the tip or ball of the thumb engaging the leading one of clips 12, which is positioned near the discharge ends at the arcuate opening 11a in the top wall 11. The lead clip 12 is pushed by the surgeon over the ramps 9, 10 and this results in pivoting the lead clip to help disengage it from the train of clips while simultaneously spreading apart not only the opposed legs of the lead clip 12, as shown in FIG. 2 but the legs of the second clip. Spreading the legs of the second clip helps to disengage the lead clip from the train of clips. As the lead clip of the train of clips passes over lips 9d, 10d and onto ramps 9 and 10 of discharge end 3 it is disengaged from the train of clips. The former second clip, now the lead clip, is retained by lips 7b, 8b against sliding back in the direction away from discharge end 3. The former lead clip 12, now the disengaged clip, is thus positioned on ramps 9, 10 with its legs in a spread-apart condition. The surgeon or operator now places the applicator adjacent the wound or incision to be clamped, with the lips of the wound or incision accommodated, if necessary, by positioning recesses 9c and 10c to receive therein the edge or lip of the wound to be closed or clamped. This facilitates the ability of the surgeon or operator to precisely position the clip. The surgeon or operator then pushes the clip 12 over the ends of discharge tips 9e, 10e of the ramps 9, 10, and onto the wound or incision. The natural resiliency of the clip 12 causes the spread-apart legs to close in clamping engagement on the wound or incision upon being pushed off the ramps 9, 10.

Figure 10:
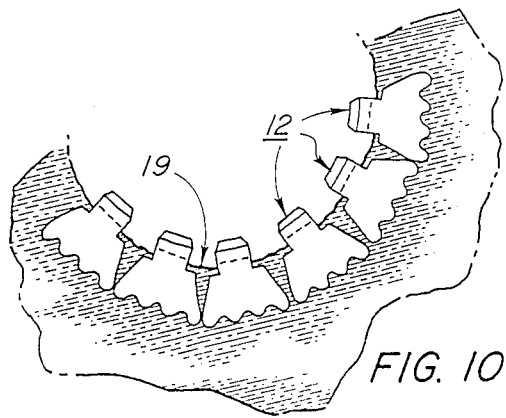
FIG. 10 is a plan view showing the arrangement of a series of the clips of FIG. 5 applied to a circular incision.

FIG. 10 illustrates the application of a series of spreadable clips 12 to the edge of a wound or incision indicated at 19. Relatively tight spacing of the clips may be attained, as illustrated, particularly on an arcuate incision such as that illustrated, because of the front-to-rear taper of the clips. (The front face of the clip is the face containing the clamping slit and the rear face is that containing the bight portion.) This shows that the spreadable clips of this invention are not only well suited for use with the surgical applicator as described herein, but have the added advantage of providing efficient and closely-positioned application to wounds or incisions of circular and other configurations.

Figure 11:
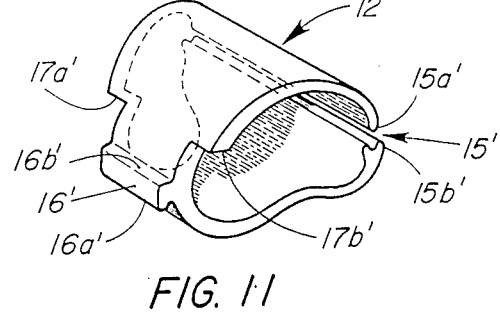
FIG. 11 is a perspective view showing the rear or bight side of another embodiment of a spreadable clip in accordance with the present invention.

Referring now to FIG. 11 there is shown another embodiment of a clip in accordance with the present invention in which parts of the clip corresponding to those of the clip of FIGS. 5-9 are correspondingly numbered, but with the addition of a prime indicator. Thus, clip 12' of FIG. 11 has formed in the bight portion thereof a land 16' which provides a groove or recess 16a' and a shoulder 16b', and has corner shoulders 17a' and 17b'. These parts are similar or identical in shape and function to the corresponding parts of the embodiment of FIGS. 5-9, and so need not be further described. However, slit 15' is seen to be of generally straight-line contour instead of having a toothed contour as do the clips of the embodiment of FIGS. 5-9. Bearing lip 15a' has a tongue extending longitudinally of slit 15' and bearing lip 15b' has a groove extending longitudinally of slit 15'. Lips 15a' and 15b' are coextensive and respectively dimensioned and configured to define a tongue-and-groove bearing surface of slit 15' to facilitate clamping living tissue or other material therebetween. The clips of FIG. 11 may conveniently be cut from an extruded member.

Referring now to FIGS. 12-14, there is illustrated another embodiment of an applicator which is generally similar in construction to the applicator of FIG. 1. Accordingly, parts of the applicator of FIG. 12 corresponding to those of the applicator of FIG. 1 are identically numbered save for the addition of a prime indicator. Thus, the applicator 1' of FIG. 12 comprises a storage enclosure 2' having a discharge end 3', a back wall 4', side walls 5' and 6', top wall 11' and a bottom wall 18'. As described with respect to the FIG. 1 embodiment, applicator 1' may be designed to be re-fillable or to be disposable, i.e, designed to be discarded after its supply of clips is exhausted. In the FIG. 12 embodiment, the applicator has but a single wedge-shaped ramp 9' which is contiguous with and extends from rail member 8'. Ramp 9' is wider in the direction transverse to the clip spreading direction at its discharge tip 9e' (FIG. 13) than at its inlet section in the vicinity of lip 9d'. Otherwise, wedge-shaped ramp 9' is generally similar in construction to ramps 9 and 10 of the FIG. 1 embodiment, having an upper ramp 9a' and a lower ramp 9b' between which is formed positioning recess 9c' (FIGS. 13 and 14). As shown in FIGS. 12, 15 and 15A, rail member 8' is, in the direction transverse to the clip-spreading direction, considerably wider than rail member 7', the width of rail member 8' being identical to the width of the inlet section of ramp 9'.

Applicator 1' uses clips 20, three of which are shown in FIGS. 14 and 14A remaining within applicator 1'. Clips 20, as best seen with reference to FIGS. 16, 16A, 16B and 16C, have opposite lateral side edges 22 and 24, one of which (22) as shown in FIG. 16A has a front-to-rear narrowing taper and the other of which (24) has a substantially untapered side edge. Clips 20 have a tooth-contoured slit 26 which is comprised of a pair of opposed bearing lips 26a, 26b. On the rear or bight portion of clip 20 is formed a land 28 which extends generally longitudinally of clip 20, generally opposite and parallel to the axis along which clamping slit 26 extends. Land 28 has opposite shoulders, one of which is recessed to define a groove 28a and the other of which defines a generally right-angled shoulder 28b, as best seen in FIG. 16B. This portion of the construction is generally similar to that described with respect to the clips of FIGS. 5-10 and so further details thereof are not required, except to note that land 28, like land 16 and 16' of the other clip embodiments, provides a rear connecting means well adapted to be releasably engaged by the front connecting means provided by bearing lips 26a and 26b. This permits releasable engagement of clips 20 into a train of clips in a manner as described above with respect to clips 12 and 12'. Clips 20 are thus seen to have a front-to-rear narrowing taper as do the other clip embodiments illustrated above, but in this case only one lateral side 22 is so tapered. As shown in FIG. 16, the untapered lateral side 24 has a guide slot 30 formed therein which is dimensioned and configured to slidably engage with rail member 7' of applicator 1'. The extreme opposite longitudinal ends of bearing lips 26a, 26b comprise engagement or bearing surfaces which, respectively, engage rail members 7' and 8'. The bearing surface provided by the longitudinal end of slit 26 on the untapered side 24 engages rail member 7' and the engagement surface provided by the longitudinal end of the slit 26 on tapered side 22 engages rail member 8' and, when the clip is pushed onto and over ramp 9', engages the latter so as to spread the clip for discharge.

The construction of clips 20 and applicator 1' permits a lateral movement of applicator 1' away from a spreadable clip 20 being applied to tissue or the like as shown by comparing FIGS. 15 and 15A. Thus, with positioning recess 9c' properly positioned adjacent to the edge of an incision or wound which is to be clamped by the spreadable clips, the clip is pushed off the discharge tip 9e' to apply clamping pressure to the tissue. The surgeon or other operator then moves the applicator 1' laterally of the applied clip to disengage the applicator from it, as shown in FIG. 15A, in which the applicator 1' is shown only partially laterally disengaged from the clip. The operator may then continue to shift the applicator 1' laterally (rightwardly as viewed in FIG. 15A) to position it to emplace the next clip without necessity of withdrawing positioning recess 9c' from the edge of the incision. This facilitates rapid movement of the applicator along the incision or wound to apply a plurality of clips as illustrated in FIG. 17. The one-side tapered clips 20 are seen in FIG. 17 to nest with each other to provide close spacing of the clips, whether along a straight, curved, circular or semi-circular incision.

As best seen with reference to FIGS. 15, 15A and 14A, it will be appreciated that the one-side tapered clips, like the two-side tapered clips of the FIGS. 5–9 embodiment, have bight portions which are narrower than the front face and dimensioned and configured to be received between the spaced-apart rail members 7' and 8'. However, in this case, the spreader comprises a single ramp member which is offset laterally relative to the longtitudinal axis of the applicator 1' and thereby facilitates lateral movement of the applicator 1' along the length of the incision because the applicator 1' need not be fully withdrawn to clear the previously emplaced clip before being laterally shifted to position the next clip laterally adjacent the previously emplaced clip.

In addition to the above-mentioned use of applying hemostatic surgical clips to control bleeding, the applicator and spreadable clips of the present invention may be used to apply spreadable clips to close a wound or generally, to apply spreadable clips to tissue for any purpose including emergency treatment or any situation in which tissue or other material must be clipped or clamped for any reason. The applicator of the present invention provides rapid application of the clips without the need to load individual clips onto an applicator one at a time. This has obvious advantages, e.g., in reducing the time required for surgical procedures, therefore reducing the time the patient must be kept under anesthesia. In some surgical procedures, as much as twenty minutes may be saved by using the applicator of the present invention instead of prior art devices requiring one-at-a-time loading of clips. The applicator of the present invention is also useable with either the left or right hand, at any angle which the surgeon or operator finds to be convenient. Further, although the applicator and spreadable clips of the present invention are well suited to be used in conjunction with each other, it will be appreciated that they may be used separately. That is, other applicators may be used to apply spreadable clips in accordance with the present invention and other clips may be applied with applicators of the present invention.

The applicator and spreadable clips of this invention may be used together or separately in a number of different applications including applying hemostatic surgical clips to control bleeding, applying spreadable clips to close a wound or incision, or generally to apply spreadable clips for any purpose.

While the invention has been described in connection with specific preferred embodiments thereof, it will be appreciated upon a reading and understanding of the foregoing, that numerous alterations and modifications to the preferred embodiments may be made which nonetheless lie within the scope of the invention and the appended claims.

What is claimed is:

1. In a spreadable surgical clip having a front face and a bight portion, a pair of opposed leg portions extending from the bight portion and terminating at their distal ends in respective bearing lips facing clamping slit in the front face of the clip, the bight portion being narrower than the front face, the improvement comprising that the clip has a front-to-rear narrowing taper which is greater on one lateral side of the clip than on the other.

2. In a spreadable surgical clip having a front face and a bight portion, a pair of opposed leg portions extending from the bight portion and terminating at their distal ends in respective bearing lips facing each other to define therebetween a longitudinally extending clamping slit in the front face of the clip, the bight portion being narrower than the front face, the improvement comprising that one lateral side only of the clip has a front-to-rear narrowing taper and the other lateral side of the clip is untapered.

3. The clip of claim 1 or claim 2 wherein the bearing lips have a toothed profile.

4. The clip of claim 3 wherein the respective toothed profiles of the bearing lips mesh one with the other.

5. The clip of claim 1 or claim 2 wherein the bearing lips are dimensioned and configured to cooperate with each other to provide therebetween a tongue-and-groove bearing surface.

6. A clip-loaded manual applicator for seriatium application of a plurality of spreadable surgical clips carried by the applicator, comprising:
a clip magazine having a clip discharge section and being dimensioned and configured to form a guideway for and releasably receive therein, a plurality of surgical clips which are spreadable in a clip-opening direction, the clip magazine comprising a storage enclosure having therein an opening adjacent to said discharge section to facilitate finger-manipulation of said clips adjacent to said discharge opening;
a spreader carried on the applicator adjacent to the clip discharge section and dimensioned and configured to receive in slidable engagement thereon for ejection therefrom spreadable clips form the clip magazine, the spreader having an inlet section disposed adjacent to the clip discharge section of the magazine and a discharge the tip which is wider in the clip-spreading direction than its inlet section, so that the spreader has a wedge-shaped profile;
a plurality of spreadable surgical clips slidably mounted within the clip magazine, each of the clips having a front face and a bight portion, a pair of opposed leg portions extending from the bight portion and terminating at their distal ends in respective bearing lips facing each other to define therebetween a clamping slit in the front face of the clip, each of the clips having a front-to-rear narrowing taper which is greater on one lateral side of the clip than on the other, the front face of the clips carrying front connecting means and the bight portions of the clips carrying rear connecting means, the front and rear connecting means being respectively dimensioned and configured so that the rear connecting means of a clip is releasably engageable with the front connecting means of another said clip immediately trailing it, with the clips releasably connected to adjacent clips in a train of clips whereby finger-manipulation of the lead clip to push it onto the spreader and then eject it therefrom, pulls the trailing clips along in the train and positions on the spreader the clip immediately trailing the ejected lead clip.

7. The applicator of claim 6 wherein only one lateral side of the clip has the front-to-rear narrowing taper and the other lateral side of the clip is untapered.

8. The applicator of claim 6 or claim 7 wherein the spreader is dimensioned and configured relative to the guideway formed by the clip magazine whereby to impose a pivoting movement on a clip slidably moved from the clip magazine onto the spreader, which pivoting movement tends to disengage the lead clip from the train of clips.

9. The applicator of claim 6 or claim 7 including a pair of laterally spaced-apart rail members within the storage enclosure, at least one of the rail members being aligned with the ramp and terminating at the inlet section thereof.

10. The applicator of claim 6 or claim 7 wherein the spreader comprises one ramp extending from one lateral side of the clip magazine.

11. The applicator of claim 6 or claim 7 wherein the spreader comprises a pair of laterally spaced-apart ramps each having a wedge-shaped profile and both longitudinally opposite ends of the front face of the clips define respective spaced-apart engagement surfaces.

12. The applicator of claim 6 or claim 7 wherein the spreader comprises one ramp member laterally off-set from the longitudinal axis of the guideway.

* * * * *